United States Patent [19]
Dupuis

[11] Patent Number: 6,071,499
[45] Date of Patent: Jun. 6, 2000

[54] COSMETIC COMPOSITION COMPRISING AN ANIONIC ACRYLIC POLYMER AND AN OXYALKYLENATED SILICONE

[75] Inventor: Christine Dupuis, Paris, France

[73] Assignee: L'Oreal, Paris, France

[21] Appl. No.: 08/815,934

[22] Filed: Mar. 13, 1997

[30] Foreign Application Priority Data

Mar. 14, 1996 [FR] France .................................. 96 03233

[51] Int. Cl.⁷ ...................................................... A61K 7/11

[52] U.S. Cl. ............................. 424/47; 424/63; 424/70.1; 424/70.11; 424/70.12; 424/70.16; 424/70.22; 424/DIG. 1; 424/DIG. 2

[58] Field of Search ............................... 424/70.1, 78.02, 424/70.11, 70.12, 70.16, 70.22, 78.03, DIG. 1, DIG. 2, 45

[56] References Cited

U.S. PATENT DOCUMENTS

| 4,311,695 | 1/1982 | Starch . | |
|---|---|---|---|
| 5,063,051 | 11/1991 | Grollier et al. | ...................... 424/70.11 |
| 5,344,643 | 9/1994 | Theil et al. . | |

FOREIGN PATENT DOCUMENTS

| 0260641 | 3/1988 | European Pat. Off. . |
|---|---|---|
| 1163113 | 6/1989 | Japan . |

*Primary Examiner*—Thurman K. Page
*Assistant Examiner*—R. Bawa
*Attorney, Agent, or Firm*—Finnegan, Henderson, Farabow, Garrett & Dunner, L.L.P.

[57] ABSTRACT

A cosmetic composition comprising in a cosmetically acceptable medium, at least one anionic acrylic polymer and at least one specific oxyalkylenated silicone, and a process for the cosmetic treatment of keratinous substances, such as the hair or eyelashes, comprising applying to the keratinous substances a cosmetic composition as defined above and optionally rinsing with water.

34 Claims, No Drawings

COSMETIC COMPOSITION COMPRISING AN ANIONIC ACRYLIC POLYMER AND AN OXYALKYLENATED SILICONE

The present invention is directed to cosmetic compositions containing, in a cosmetically acceptable medium, at least one fixing anionic acrylic polymer and at least one specific oxyalkylenated silicone.

The present invention is also directed to a process for the cosmetic treatment of keratinous substances, such as the hair or eyelashes, comprising the step of applying to the keratinous substances a cosmetic composition as defined above, and optionally rinsing with water.

Hair shaping or form retention compositions containing styling polymers, i.e., fixing polymers, in their formulation are generally disadvantageous because they make it difficult to disentangle, restyle or brush the hair, in particular during blow-drying.

In addition, certain polymers exhibit the disadvantage of powdering on the hair, i.e., presence of white films, during brushing or combing after the polymer has dried.

The combination of silicone derivatives with fixing polymers is known in cosmetic compositions for form retention and/or fixing of the hairstyle. It has been found that these silicone derivatives improve the properties of disentangling, softness and sheen of hair treated using these compositions. However, silicone derivatives are not favorable to the styling and/or fixing properties of compositions containing fixing polymers and, at the same time, the disentangling and softness properties are not yet satisfactory.

The aim of the present invention is therefore to provide compositions which make it possible to fix and/or to shape the hairstyle, which have good fixing power and good shape retaining properties over time and contribute good feel and disentangling properties. Moreover, they must form an invisible deposit on the hair and must not powder during brushing or combing.

Applicant has discovered that cosmetic compositions containing, in a cosmetically acceptable medium, at least one anionic acrylic polymer and at least one specific oxyalkylenated silicone, unexpectedly and surprisingly, make it possible to obtain the properties described above, in particular a decrease in powdering, a more natural feel and good shape retention of the hairstyle over time.

A subject of the present invention is thus a new cosmetic composition, comprising, in a cosmetically acceptable medium, at least one anionic fixing polymer derived from acrylic or methacrylic acid and at least one specific oxyalkylenated silicone described herein below.

In the context of the present invention, the expression "fixing polymer" is understood to refer to any polymer which has, as its main function, temporarily fixing of the shape of the hairstyle.

The anionic fixing polymer derived from acrylic or methacrylic acid which can be used according to the present invention is preferably selected from the following polymers:

(A) homopolymers of acrylic or methacrylic acid or their salts and in particular the products sold under the names VERSICOL E or K by the company Allied Colloid; and (B) copolymers of at least one acrylic and/or methacrylic acid with at least one monoethylenic monomer, such as ethylene, styrene, vinyl esters, optionally N-substituted acrylamides or methacrylamides, acrylic or methacrylic acid esters or vinyllactams, optionally crosslinked, such as those described in particular in French Patent No. 1,222,944 and German Application No. 2,330,956, the disclosures of which are incorporated herein by reference, the copolymers of this type containing in their chain an optionally N-alkylated and/or -hydroxyalkylated acrylamide unit, such as those described in particular in Luxembourg Patent Applications 75370 and 75371, the disclosures of which are incorporated herein by reference, or provided under the name QUADRAMER by the Company American Cyanamid.

Mention may preferably be made, among these polymers, of the following:

copolymers of acrylic acid and of linear or branched $C_1$–$C_4$ alkyl methacrylate;

copolymers of methacrylic acid and of linear or branched $C_1$–$C_4$ alkyl acrylate, such as copolymers of methacrylic acid and of ethyl acrylate, for example LUVIMER MAE sold by the company BASF;

copolymers of acrylic acid and of linear or branched $C_1$–$C_4$ alkyl acrylate, such as, for example, copolymers of acrylic acid and of ethyl acrylate, for example ACRYSOL 33 provided by Rohm & Haas;

copolymers of methacrylic acid and of linear or branched $C_1$–$C_4$ alkyl methacrylate, such as, in particular, copolymers of methacrylic acid and of methyl methacrylate;

copolymers of (meth)acrylic acid, of linear or branched $C_1$–$C_{20}$ alkyl (meth)acrylate and of vinylpyrrolidone, such as that sold by the company ISP under the name ACRYLIDONE LM, those sold by the company BASF under the names LUVIFLEX VBM 35 and LUVIFLEX VBM 70, or those sold under the name STEPANHOLD EXTRA by the company Stepan;

(meth)acrylic acid/ethyl acrylate/tert-butyl acrylate copolymers, such as the product sold under the name LUVIMER 100 P by the company BASF;

(meth)acrylic acid/alkyl acrylate/alkyl methacrylate copolymers, in particular the ethyl acrylate/methyl methacrylate/methacrylic acid/acrylic acid copolymer, such as the product sold under the name AMERHOLD DR 25 by the company Amerchol;

copolymers of (meth)acrylic acid and of at least one acrylamide which are optionally N-substituted, sold for example under the names RETEN 421, 423 or 425 by the Company Hercules or under the names ULTRAHOLD by the company BASF;

copolymers of (meth)acrylic acid and of styrene; and copolymers of (meth)acrylic acid and of vinylpyrrolidone, such as that sold under the name ACRYLIDONE ACP 1001 by the company ISP.

The anionic fixing polymers are more preferably selected from the acrylic acid/ethyl acrylate/N-tert-butylacrylamide copolymers sold under the name ULTRAHOLD STRONG by the company BASF, the copolymers of methacrylic acid and of methyl methacrylate sold under the name EUDRAGIT L by the company Rohm Pharma, the copolymer of methacrylic acid and of ethyl acrylate sold under the name LUVIMER MAEX or MAE by the company BASF, or the vinylpyrrolidone/acrylic acid/lauryl methacrylate copolymer sold under the name ACRYLIDONE LM by the company ISP.

The oxyalkylenated silicones used in accordance with the present invention are preferably selected from the compounds of formula (I):

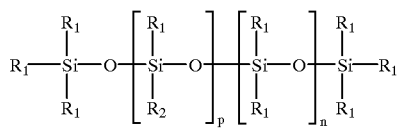

wherein:

$R_1$, which may each be identical or different, represents a hydrogen atom, a linear or branched $C_1$–$C_{30}$ alkyl radical or a phenyl radical;

$R_2$, which is identical or different, represents —$(C_xH_{2x})$—$(OC_2H_4)_a$—$(OC_3H_6)_b$—$OR_3$;

$R_3$, which is identical or different, is a hydrogen atom, a linear or branched alkyl radical having from 1 to 12 carbon atoms or a linear or branched acyl radical having from 2 to 12 carbon atoms;

n ranges from 100 to 1000;
p ranges from 1 to 8;
a ranges from 0 to 50;
b ranges from 0 to 50;
a+b is greater than or equal to 1; and
x ranges from 1 to 5;

the number-average molecular weight being greater than or equal to 15,000 and preferably ranging from 25,000 to 75,000.

Use is preferably made of the oxyalkylenated silicones of formula (I) which correspond to at least one, and more preferably to all, of the following conditions:

$R_1$ represents a methyl radical;

$R_3$ represents a hydrogen atom, a methyl radical or an acetyl radical, and more preferably hydrogen;

p ranges from 2 to 6;
a ranges 5 to 40, and preferably from 15 to 30;
b ranges 5 to 40, and preferably from 15 to 30;
x is equal to 2 or 3; and
n ranges from 200 to 600, and preferably from 300 to 500.

Such silicones are, for example, described in U.S. Pat. No. 4,311,695, the disclosure of which is incorporated herein by reference.

The most particularly preferred silicones are, for example, those sold as a 10% by weight solution in a cyclomethicone (Dow Corning 344) under the tradename FLUID DC 3225 C by the company Dow Corning.

The anionic fixing polymer or polymers are generally present in amounts ranging from 0.1% to 20% by weight, and preferably in amounts ranging from 1% to 10% by weight with respect to the total weight of the composition.

The oxyalkylenated silicone or silicones can be present in amounts ranging from 0.001% to 10% by weight, and preferably in amounts ranging from 0.005% to 3% by weight with respect to the total weight of the composition.

The cosmetically acceptable medium generally comprises solvents which are compatible with the fixing polymer and the oxyalkylenated silicone. These solvents are, for example, water, alcohols or acetone, which can be used alone or as a mixture.

Use is preferably made of $C_1$–$C_6$ alcohols as the solvent. Mention may preferably be made, among the alcohols, of ethanol, isopropanol, polyalcohols, such as diethylene glycol, or glycol ethers, such as the monoalkyl ethers of glycol, of diethylene glycol, of propylene glycol or of dipropylene glycol. Ethanol is particularly preferred.

The compositions according to the invention are preferably formulated without water, i.e., they contain less than 8% by weight of water with respect to the total weight of the composition and more preferably less than 5%. The compositions thus dry more quickly.

The composition of the invention can also contain at least one additive selected from thickeners, fatty acid esters, esters of fatty acids and of glycerol, silicones, surfactants, fragrances, preservatives, sun screening agents, proteins, vitamins, polymers, vegetable, animal, mineral or synthetic oils and any other additive conventionally used in the cosmetics field.

These additives are preferably present in the compositions according to the invention in proportions which can range from 0 to 40% by weight with respect to the total weight of the composition. The precise amount of each additive depends on its nature and is easily determined by the person skilled in the art.

Of course, the person skilled in the art will take care to choose the possible compound or compounds to be added to the composition according to the invention so that the advantageous properties intrinsically attached to the composition in accordance with the invention are not, or not substantially, detrimentally affected by the envisaged addition.

The compositions according to the invention can be provided in the form of gels, milks, creams, dispersions, emulsions, more or less thickened lotions or foams.

The compositions according to the invention are more preferably used as leave-in products, in particular for form retention of the hairstyle or shaping or styling the hair. Even more preferably the compositions in accordance with the invention are hair-setting lotions, blow-drying lotions, fixing compositions (lacquers) and styling compositions. The lotions can be packaged in various forms, in particular, in vaporizers or pump-action sprays or in aerosol containers, in order to provide for application of the composition in vaporized form or in the form of a foam. Such packaging forms are indicated, for example, when it is desired to obtain a spray, a lacquer or a foam for fixing or treating the hair.

When the composition according to the invention is packaged in the form of an aerosol for the purpose of obtaining a lacquer or an aerosol foam, it comprises at least one propellant which can be selected from volatile hydrocarbons, such as n-butane, propane, isobutane, a chlorinated and/or fluorinated hydrocarbon and their mixtures. Use may also be made, as a propellant, of carbon dioxide gas, nitrous oxide, dimethyl ether, nitrogen, compressed air and their mixtures.

The concentration of propellant generally ranges from 10 to 90% by weight with respect to the total weight of the pressurized composition and preferably from 15 to 70% by weight with respect to the total weight of the composition.

A further subject of the invention is a process for the cosmetic treatment of keratinous substances, such as the hair or eyelashes, which comprises the application on the latter of a composition as defined above and then, optionally, an operation of rinsing with water.

The invention will now be illustrated more fully by means of the following examples, which should not be regarded as limiting it to the embodiments described. In the following, "AM" means Active Material.

EXAMPLE 1

A fixing spray composition according to the invention, packaged in a pump-action spray, was prepared with the following composition:

| | |
|---|---|
| Methacrylic acid/ethyl acrylate/tert-butyl acrylate terpolymer sold under the name Luvimer 100 P by the company BASF | 7 g |
| 2-Amino-2-methyl-1-propanol | q.s. for 100% neutralization of the polymer |
| Oxyalkylenated silicone sold, containing 10% of AM, under the name FLUID DC 3225C by the company Dow Corning | 0.05 g AM |
| Ethanol | q.s. for 100 g |

This composition was applied, after blow-drying, to washed and dried hair. The hair was maintained in shape naturally and easily disentangled without powdery residues. The hair had a pleasant natural feel.

EXAMPLE 2

A fixing spray composition (A), packaged in an aerosol container, was prepared with the following composition:

| | |
|---|---|
| Acrylic acid/ethyl acrylate/N-tert-butyl-acrylamide terpolymer sold under the name ULTRAHOLD STRONG by the company BASF | 8 g |
| 2-Amino-2-methyl-1-propanol | q.s. for 100% neutralization of the polymer |
| Oxyalkylenated silicone sold, containing 10% of AM, under the name FLUID DC 3225C by the company Dow Corning | 0.06 g AM |
| Ethanol | q.s. for 100 g |
| Pressurization scheme: | |
| Above composition: | 37 g |
| Dimethyl ether | 43 g |
| Pentane | 20 g |

37 g of the above composition were introduced into an aerosol container, a valve was crimped on and then the dimethyl ether and the pentane were introduced. The composition exhibited the same properties as those of Example 1.

A composition (B), identical to composition (A), was prepared in which the acrylic polymer according to the invention (ULTRAHOLD STRONG) was replaced by the same amount of a polymer of crotonic type (crotonic acid/vinyl acetate/vinyl tert-butylbenzoate terpolymer).

Each of these compositions was applied to washed and dried hair. A panel of 5 experienced testers evaluated the properties of each composition.

Hair treated with the composition (A) according to the invention had a more natural and softer feel. Composition (A) did not powder on the hair after drying and combing. Moreover, the lacquering power of composition (A) was greater than that of composition (B).

EXAMPLE 3

A fixing spray composition (C), packaged in an aerosol container, was prepared with the following composition:

| | |
|---|---|
| Acrylic acid/ethyl acrylate/N-tert-butylacrylamide terpolymer sold under the name ULTRAHOLD STRONG by the company BASF | 6.1 g |
| 2-Amino-2-methyl-1-propanol | q.s. for 100% neutralization of the polymer |
| Oxyalkylenated silicone sold, containing 10% of AM in a cyclomethicone, under the name FLUID DC 3225C by the company Dow Corning | 0.043 g AM |
| Ethanol | q.s. for 100 g |
| Pressurization scheme: | |
| Above composition: | 53 g |
| Dimethyl ether | 15 g |
| Butane | 32 g |

53 g of the above composition were introduced into an aerosol container, a valve was crimped on and then the dimethyl ether and the butane were introduced. The composition exhibited the same properties as those of Example 1.

In the same way, a composition (D), not in accordance with the invention, was prepared with the following composition:

| | |
|---|---|
| Acrylic acid/ethyl acrylate/N-tert-butylacrylamide terpolymer sold under the name ULTRAHOLD STRONG by the company BASF | 6.1 g |
| 2-Amino-2-methyl-1-propanol | q.s. for 100% neutralization of the polymer |
| Oxyalkylenated silicone sold under the name FLUID DC 190 by the company Dow Corning | 0.043 g AM |
| Cyclomethicone | 0.387 g |
| Ethanol | q.s. for 100 g |
| Pressurization scheme: | |
| Above composition: | 53 g |
| Dimethyl ether | 15 g |
| Butane | 32 g |

Each of these compositions was applied to washed and dried hair. A panel of 5 experienced testers evaluated the properties of each composition.

Hair treated with composition (C) according to the invention had a more natural and soft feel than that treated with composition (D).

EXAMPLE 4

A fixing spray composition, packaged in an aerosol container, was prepared with the following composition:

| | |
|---|---|
| Acrylic acid/ethyl acrylate/N-tert-butylacrylamide terpolymer sold under the name ULTRAHOLD STRONG by the company BASF | 7 g |
| 2-Amino-2-methyl-1-propanol | q.s. for 100% neutralization of the polymer |
| Oxyalkylenated silicone sold under the name FLUID DC 3225C by the company Dow Corning | 0.03 g AM |
| Water | 5 g |
| Ethanol | q.s. for 100 g |
| Pressurization scheme: | |
| Above composition: | 45 g |
| Dimethyl ether | 55 g |

37 g of the above composition were introduced into an aerosol container, a valve was crimped on and then the dimethyl ether and the pentane was introduced.

This composition exhibited the same properties as those of Example 1.

What is claimed is:

1. A cosmetic composition, comprising, in a cosmetically acceptable medium, at least one anionic fixing polymer derived from acrylic or methacrylic acid and at least one oxyalkylenated silicone of formula (I):

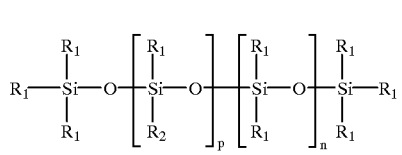

wherein:
- each $R_1$, which is identical or different, represents a hydrogen atom, a linear or branched $C_1$–$C_{30}$ alkyl radical or a phenyl radical;
- $R_2$ which is identical or different, represents —$(C_xH_{2x})$—$(OC_2H_4)_a$—$(OC_3H_6)_b$—$OR_3$;
- $R_3$ which is identical or different, represents a hydrogen atom, a linear or branched alkyl radical having from 1 to 12 carbon atoms or a linear or branched acyl radical having from 2 to 12 carbon atoms;
- n ranges from 100 to 1000;
- p ranges from 1 to 8;
- a ranges from 0 to 50;
- b ranges from 0 to 50;
- a+b is greater than or equal to 1; and
- x ranges from 1 to 5;

wherein the number-average molecular weight of said at least one oxyalkylated silicone is greater than or equal to 15,000.

2. A composition according to claim 1, wherein said at least one oxyalkylenated silicone satisfies at least one of the following conditions:
- $R_1$ represents a methyl radical;
- $R_3$ represents a hydrogen atom, a methyl radical or an acetyl radical;
- p ranges from 2 to 6;
- a ranges from 5 to 40;
- b ranges from 5 to 40;
- x is equal to 2 or 3; or
- n ranges from 200 to 600.

3. A composition according to claim 2, wherein $R_3$ represents a hydrogen atom.

4. A composition according to claim 2, wherein a ranges from 15 to 30.

5. A composition according to claim 2, wherein b ranges from 15 to 30.

6. A composition according to claim 2, wherein n ranges from 300 to 500.

7. A composition according to of claim 1, wherein said at least one oxyalkylenated silicone has a number-average molecular weight ranging from 25,000 to 75,000.

8. A composition according to claim 1, wherein said at least one anionic fixing polymer is present in an amount ranging from 0.1% to 20% with respect to the total weight of the composition.

9. A composition according to claim 8, wherein said at least one anionic fixing polymer is present in an amount ranging from 1% to 10% by weight with respect to the total weight of the composition.

10. A composition according to claim 1, wherein said at least one oxyalkylenated silicone is present in an amount ranging from 0.001% to 10% by weight with respect to the total weight of the composition.

11. A composition according to claim 10, wherein said at least one oxyalkylenated silicone is present in an amount ranging from 0.005% to 3% by weight based on the total weight of the composition.

12. A composition according to claim 1, wherein said at least one anionic fixing polymer is:
   (A) a homopolymer of acrylic or methacrylic acid or one of their salts; or
   (B) a copolymer of at least one acrylic and/or methacrylic acid with at least one monoethylenic monomer.

13. A composition according to claim 12, wherein said at least one monoethylenic monomer is ethylene, styrene, a vinyl ester, an optionally N-substituted acrylamide or methacrylamide, an acrylic or methacrylic acid ester or vinyllactam.

14. A composition according to claim 12, wherein said at least one anionic fixing polymer is a:
- copolymer of acrylic acid and of linear or branched $C_1$–$C_4$ alkyl methacrylate;
- copolymer of methacrylic acid and of linear or branched $C_1$–$C_4$ alkyl acrylate;
- copolymer of acrylic acid and of linear or branched $C_1$–$C_4$ alkyl acrylate;
- copolymer of methacrylic acid and of linear or branched $C_1$–$C_4$ alkyl methacrylate;
- copolymer of (meth)acrylic acid, of linear or branched $C_1$–$C_{20}$ alkyl (meth)acrylate and of vinylpyrrolidone;
- (meth)acrylic acid/ethyl acrylate/tert-butyl acrylate copolymer;
- (meth)acrylic acid/alkyl acrylate/alkyl methacrylate copolymer;
- copolymer of (meth)acrylic acid and of at least one acrylamide which may be N-substituted;
- copolymer of (meth)acrylic acid and of styrene; or
- copolymer of (meth)acrylic acid and of vinylpyrrolidone.

15. A composition according to claim 14, wherein said at least one anionic fixing polymer is a copolymer of methacrylic acid and of methyl methacrylate.

16. A composition according to claim 14, wherein said at least one anionic fixing polymer is a:
- acrylic acid/ethyl acrylate/N-tert-butyl-acrylamide copolymer;
- copolymer of methacrylic acid and of methyl methacrylate;
- copolymer of methacrylic acid and of ethyl acrylate;
- copolymer of acrylic acid and of $C_1$–$C_4$ alkyl methacrylate;
- copolymer of vinylpyrrolidone, of acrylic acid and of $C_1$–$C_{20}$ alkyl methacrylate;
- methacrylic acid/ethyl acrylate/tert-butyl acrylate copolymer;
- alkyl acrylate/alkyl methacrylate/acrylic acid copolymer; or
- ethyl acrylate/methyl methacrylate/methacrylic acid/acrylic acid copolymer.

17. A composition according to claim 1, wherein said cosmetically acceptable medium comprises at least one $C_1$–$C_6$ alcohol.

18. A composition according to claim 17, wherein said at least one $C_1$–$C_6$ alcohol is ethanol, isopropanol or polyalcohol.

19. A composition according to claim 18, wherein said polyalcohol is a diethylene glycol or a glycol ether.

20. A composition according to claim 18, wherein said glycol ether is a monoalkyl ether of glycol, of diethylene glycol, of propylene glycol or of dipropylene glycol, or a mixture thereof.

21. A composition according to claim 1, which is in the form of a gel, a milk, a cream, a dispersion, a thickened lotion or a foam.

22. A composition according to claim 1, wherein said composition is a product for styling, for form retention of a hairstyle or for hair shaping.

23. A composition according to claim 1, which is packaged in the form of a vaporizer, a pump-action spray, a spray aerosol container, a lacquer or a foam.

24. A composition according to claim 1, further comprising a propellant.

25. A composition according to claim 24, wherein said propellant is present in an amount ranging from 10% to 90% by weight with respect to the total weight of the composition.

26. A composition according to claim 25, wherein said propellant is present in an amount ranging from 15% to 70% by weight with respect to the total weight of the composition.

27. A composition according to claim 24, wherein said propellant is a volatile hydrocarbon.

28. A composition according to claim 27, wherein said volatile hydrocarbon is n-butane, propane, isobutane, a chlorinated and/or fluorinated hydrocarbon, carbon dioxide gas, nitrous oxide, dimethyl ether, nitrogen, compressed air or a mixture thereof.

29. A composition according to claim 1, which contains less than 8% by weight of water, with respect to the total weight of the composition.

30. A composition according to claim 29, which contains less than 5% by weight of water, with respect to the total weight of the composition.

31. A process for the cosmetic treatment of keratinous substances, said process comprising the step of applying to said keratinous substances an effective amount of a composition according to claim 1.

32. A process according to claim 20, wherein said keratinous substance is hair.

33. A process for styling or shaping hair, said process comprising the step of applying to said hair an effective amount of a composition according to claim 1.

34. A process for retaining the form of styled hair, said process comprising the step of applying to said styled hair an effective amount of a composition according to claim 1.

* * * * *